(12) United States Patent
Crawford et al.

(10) Patent No.: US 7,854,888 B2
(45) Date of Patent: Dec. 21, 2010

(54) METHODS FOR DETERMINING EFFECTIVENESS OF WASTE WATER TANK DEODORIZERS AND SYNTHETIC WASTE COMPOSITIONS FOR USE IN SAID METHODS

(75) Inventors: Nancy Diann Crawford, Great Bend, KS (US); David Lee Nachtigal, Great Bend, KS (US); Lewis Lynn Gray, Great Bend, KS (US)

(73) Assignee: Fuller Brush Company, Inc., Great Bend, KS (US)

( * ) Notice: Subject to any disclaimer, the term of this patent is extended or adjusted under 35 U.S.C. 154(b) by 496 days.

(21) Appl. No.: 11/998,335

(22) Filed: Nov. 29, 2007

(65) Prior Publication Data

US 2008/0131310 A1    Jun. 5, 2008

Related U.S. Application Data

(60) Provisional application No. 60/872,756, filed on Dec. 4, 2006.

(51) Int. Cl.
*A61L 2/24* (2006.01)
*A61L 9/00* (2006.01)
(52) U.S. Cl. ............................................. 422/3; 422/5
(58) Field of Classification Search ..................... 422/3, 422/5
See application file for complete search history.

(56) References Cited

U.S. PATENT DOCUMENTS 6,365,723 B1   4/2002   Blattner et al.
6,495,096 B1 *  12/2002   Hamaguchi et al. ............ 422/5
6,817,317 B2   11/2004   Ito et al.
2005/0141966 A1   6/2005   Greene
2006/0140817 A1   6/2006   Cumberland et al.
2006/0246040 A1   11/2006   Ebisawa et al.

OTHER PUBLICATIONS

German Blue Angel Award Program No. RAL-UZ84a Award Criteria Annex 2 Test Method for Determining the Serviceability of Sanitary Additives for Odor Control in Mobile Toilets Feb. 2005.
US Environmental Protection Agency, "OPPTS 850.6800 Modified Activated Sludge, Respiration Inhibition Test for Sparingly Soluble Chemicals", Ecological Effects Test Guidelines, EPA 712-C, pp. 96-168, Apr. 1996.

* cited by examiner

*Primary Examiner*—Sean E Conley
*Assistant Examiner*—Kevin C Joyner
(74) *Attorney, Agent, or Firm*—Simpson & Simpson, PLLC

(57) ABSTRACT

A method for determining the effectiveness of a waste water tank deodorizer includes the steps of (i) providing a synthetic waste water media and a hydrogen sulfide generating microorganism; (ii) introducing in any order to the synthetic waste water media the hydrogen sulfide generating microorganism and a waste water tank deodorizer to be tested, and (iii) measuring the time or delay for the generation of hydrogen sulfide to occur beginning with combining of the hydrogen sulfide generating microorganism, the waste water tank deodorizer and the synthetic waste water media. Alternatively, measurement is also disclosed involving the number of bacteria present in the waste water during the test period. The invention includes a novel synthetic waste composition for use in the above method comprising at least a peptone, an animal protein extract, urea or a urea-containing compound, a metallic salt, a fiber-containing grain product and a cellulose-containing product.

19 Claims, No Drawings

US 7,854,888 B2

METHODS FOR DETERMINING EFFECTIVENESS OF WASTE WATER TANK DEODORIZERS AND SYNTHETIC WASTE COMPOSITIONS FOR USE IN SAID METHODS

CROSS REFERENCE TO RELATED APPLICATION

This application claims the benefit of U.S. Provisional Application 60/872,756, filed Dec. 4, 2006.

TECHNICAL FIELD

This invention relates generally to methods for determining or measuring the effectiveness of waste water tank deodorizers used in waste matter holding tanks commonly employed in recreational vehicles, boats, portable toilets and other similar structures. The invention also relates to novel synthetic waste water media/compositions employed in the above methods for determining the effectiveness of waste water tank deodorizers.

BACKGROUND OF THE INVENTION

Sanitary waste storage devices found in recreational vehicles, travel trailers, camping structures, boats, and other portable toilet facilities, such as commonly found at camp grounds, construction sites, temporary bathroom facilities for large public gatherings, like sporting events, natural disaster points, etc., comprise sanitary waste water systems and tanks for the capture, retention and containment of human waste matter until such time as it can be transported to a central "dumping station". Typically, at the dumping station the waste matter is piped to a sewage treatment system. While solid and liquid waste matter is held, they will naturally degrade in a limited fashion aerobically, but quickly degrade anaerobically due to high soil levels within the waste water tank, and due to the low levels of aeration in such tanks compared to open pipe systems.

A further significant factor in the degradation process, and the resulting developing odors in portable waste storage systems is the concentration of waste compounds stored in holding tanks is often much greater than in sanitary waste systems found in homes and city sewage systems. This is often due to the limited use of water in portable sanitary systems. In comparison, home sewage systems routinely operate with much more water content, which allows for greater aeration in transmission throughout sewerlines. In addition, mean summer time temperatures accelerate degradation in waste tanks exposed to open, ambient air temperatures, where temperatures can average more than 30° C.

Especially under anaerobic conditions, degradation of waste matter becomes exacerbated by the foregoing factors resulting in the rapid discharge of noxious odors/fumes. The prevention or limiting of these noxious odors/fumes is vital to the performance and effectiveness of additives in deodorizing waste water. At a certain point in the normal degradation of waste, odor emission becomes unacceptable for normal occupation of temporary and/or portable structures where the waste water tanks are stationed.

While most waste water tank deodorizing compositions appear to provide some level of inhibition, retardation and/or masking of odor build-up due to the generation of hydrogen sulfide gas in the process, their performance has not been readily determinable by objective comparative testing protocols. Consequently, measurable and reliable performance standards of waste water tank deodorizer products have been limited principally to less reliable subjective evaluation standards.

A waste water holding tank is commonly expected to hold waste compounds for five days. The traditional method of controlling odor during this five day holding period has been through the use of formalin solutions. The conventional wisdom has been to include 400-600 ppm formaldehyde at peak tank capacity. The art has expanded in the use of less hazardous materials than formaldehyde, but their introduction has been the result of much trial and error performance evaluation. Consequently, there has been very little verifiable data to prove efficacy, or basis for developing and optimizing performance, or for formulating better performing waste water tank deodorizers.

Standardized test methods to determine efficacy of a deodorizing compound are sparse in the art with the exception of the German Blue Angel Award Program number RAL-UZ 84a Award Criteria Annex 2 Test Method for determining the Serviceability of Sanitary Additives for Odor Control in Mobile Toilets dated February 2005. This method is quite difficult and expensive to perform due to its procedure and conditions that must be performed. The German Blue Angel Program requires 10 people to rate the odor subjectively on a level of disagreeability. Also, the Program is potentially an unsafe procedure because it requires the use of swine feces. Subjective personal preference as to disagreeability of odors would also be more preferably replaced with a more quantifiable objective method.

As pointed out above, state of the art methods have relied principally on deodorizer technologies comprising formalin solutions supplied at about 50-100% formalin or approximately 18-37% formaldehyde. Other antimicrobials that have been used as waste water tank deodorizers have included quaternary ammonium compounds such as BTC® series (a registered trademark of the Stepan Company Northfield, Ill.) and Bardac® or Barquat® (both a registered trademark of Lonza Inc, Allendale, N.J.); or other compounds such as Dowicil® (a registered trademark of The Dow Chemical Company of Midland, Mich.) or Bronopol® (2-bromo-2-nitropropane-1,3-diol). Some non-antimicrobial additives include various nitrate salts, and bacterial or enzyme suspensions.

However, there still remains an unfulfilled need for an accurate and reliable scientific method for objective testing and evaluating the performance of waste water tank deodorizers formulated with the goal of modifying, retarding or inhibiting the degradation of waste products and generation of odoriferous and potentially hazardous compounds, e.g., hydrogen sulfide gas.

Likewise, there is also a need for an adjunct synthetic/surrogate waste water composition that can perform as a standardized test media and substitute for biohazardous natural waste material currently used in testing and evaluating the performance of waste water tank deodorizers.

SUMMARY OF THE INVENTION

It is therefore a principal object of the invention to provide an objective method for determining the effectiveness of waste water tank deodorizers. The method includes the steps of:

(i) providing a synthetic waste water media and a hydrogen sulfide generating microorganism;

(ii) introducing in any order to the synthetic waste water media, the hydrogen sulfide generating microorganism and the waste water tank deodorizer to be tested, and (iii) measuring the time or delay for the generation of hydrogen sulfide to occur beginning with combining of the hydrogen sulfide generating microorganism, the waste water tank deodorizer and the synthetic waste water media.

The method may be practiced with virtually any available hydrogen sulfide generating microorganism that may be pathogenic, however, non-pathogenic bacterium are preferred. This would include such representative examples of bacterium from the family Enterobacteriaceae, enteric bacteria The microorganism from the bacterial family, Enterobacteriaceae, would include the genus *Escherichia*. Representative specie of the genus *Escherichia* would include, for example, *E. coli*. A particularly preferred representative example of a non-pathogenic hydrogen sulfide generating microorganism would be *E. coli*, strain K12 (ATCC 25253).

It is yet a further principal object of the invention to provide for novel synthetic waste water media compositions, particularly for use in the above methods for objectively measuring the performance of waste water tank deodorizers, for use as a surrogate in place of potentially more hazardous animal waste matter. The synthetic, less hazardous waste water tank media is an aqueous composition generally comprising at least a peptone, an animal protein extract, urea or a urea-containing compound, at least one metal salt; a fiber-containing grain product and a cellulose-containing paper product.

Representative peptones of the foregoing synthetic waste water media may include, for instance, a bacto peptone, proteose peptone, soytone, tryptone, to name but a few. In addition to peptone, the waste water tank deodorizer employs animal protein extract which may be a desiccated meat extract, such as a beef extract, powdered beef heart, powdered beef liver and mixtures thereof.

Urea and urea-containing compounds are intended to include not just urea, but various derivatives, including such representative examples as methyl urea, 1,3-diethylurea, thiourea, to name but a few.

Other ingredients of the synthetic waste water media include at least one metal salt, but more preferably a combination of metallic salts, which may include alkali metal salts, alkaline earth metal salts, as well as mixtures of the same. More specific representative salts include, for instance, sodium chloride, calcium chloride, magnesium sulfate, dibasic potassium phosphate and mixtures thereof.

In addition to the foregoing ingredients, the synthetic waste water media compositions of the invention include fibrous material which may be derived from various grain products, such as oats and/or corn. Other ingredients include cellulose-containing paper product, such as toilet paper and/or facial tissue.

Accordingly, the synthetic waste water media may comprise from about 4.0 to about 6.0 percent-by-weight peptone; from about 2.0 to about 4.0 percent-by-weight meat extract; from about 1.0 to about 2.0 percent-by-weight of urea or urea-derivatives or urea-containing compound; from about 0.20 to about 0.50 percent-by-weight sodium chloride; from about 0.10 to about 0.30 percent-by-weight calcium chloride; from about 0.05 to about 0.20 percent-by-weight magnesium sulfate; from about 1.0 to about 2.0 percent-by-weight dibasic potassium sulfate; from about 6.0 to about 8.0 percent-by-weight fiber-containing grain; from about 0.5 to about 2.0 percent-by-weight cellulose-containing paper product, and sufficient water to 100 percent.

It is yet a further object of the invention, that in carrying out the process of determining the effectiveness of a proposed waste water tank deodorizer that the method include the step of introducing the hydrogen sulfide generating microorganism having a verified count of bacterium of at least $\log^8$ colony forming units/ml in liquid culture media. This verified count of bacterium is introduced into the waste water for testing in an amount of at least 5.0 ml liquid culture per 500 grams of synthetic waste water media. The method includes a verified count of bacterium introduced into the waste water that produces a final organism count of not less than $\log^4$ colony forming units/ml in the synthetic waste water media.

In actual practice, the method of the invention provides for the step wherein the concentration of waste water deodorizer introduced for testing is an amount proportional to the intended end-use amount of the product in real application; wherein a usage of about 2.0 to about 40.0 fluid ounces of deodorant per 40 gallon waste tank would equal about 0.19 to about 3.91 ml of the waste water deodorant per 500 grams synthetic waste water media.

In addition to the methods discussed above, it is still a further principal object of the invention to provide novel, non-hazardous, synthetic compositions particularly well suited for use as a surrogate or substitute for hazardous natural waste in methods like those previously disclosed hereinabove, for measuring the performance or effectiveness of deodorizers for waste water.

Accordingly, the present invention provides for aqueous synthetic waste compositions comprising at least a peptone, an animal protein extract, urea or a urea-containing compound, a metallic salt, a fiber-containing grain product and a cellulose-containing product.

More specifically, the aqueous synthetic waste compositions are characterized wherein the peptone may be virtually any known and available peptone, including such representative examples as bacto peptone, proteose peptone, soytone, tryptone, and the like. The animal protein extract of the composition may be a desiccated meat extract, such as beef extract, powdered beef heart, powdered beef liver and mixtures of the same. Urea or urea-containing compound is employed, such as methyl urea, 1,3-diethylurea, thiourea, and so on. The metallic salts may comprise alkali metal salts and/or alkaline earth metal salts, such as sodium chloride, calcium chloride, magnesium sulfate, dibasic and potassium phosphate. The fiber-containing grain may be derived from oats or corn, and the cellulose-containing paper product may be a toilet paper or facial tissue, for example.

These and other features and advantages will become more apparent after a reading of the following more detailed description of the invention.

DETAILED DESCRIPTION OF THE INVENTION

The present invention broadly comprises standardized methods/procedures for the evaluation of options for treating waste water holding tanks. The present invention further comprises an improved, less hazardous waste media compositions preferably used in the standardized efficacy procedures in testing/measuring the performance particularly of deodorizers for waste water and waste water tanks.

Efficacy Protocol

A quantifiable means to monitor the progress of waste degradation would be a desirable advance in the art in order to assess the performance of a waste water tank deodorizer or additive on the degradation rate of waste or in the emission of noxious odors.

Three basic indicators are used as part of the procedure to monitor the progress of the degradation and odor emanation in the surrogate waste tank. One indicator is to simply monitor the amount and growth of the bacteria present. As the bacteria grow and multiply, the food source (waste) begins to degrade and waste odor by-products increase. The second indicator we have found useful is that of monitoring the gas by-products content in the head space of the tank system. Hydrogen sulfide is the most common and easily analyzed gas found emanating from the waste matter. Hydrogen sulfide is one of the very odorous gases emitted and is a direct indicator of the odor levels being generated as degradation proceeds. The third indicator is simply the olfactory nature of the head space of the waste tank. By ranking the degree to which it is disagreeable, a direct determination can be made to the extent of degradation, which is akin to a user determining it is time to discharge the waste holding tank.

The third indicator of ranking olfactory disagreeability is used to calibrate the first two indicators, providing alternative, quantifiable tools for the measurement of the degradation of waste materials to correspond to a real world olfactory measure. The use of olfactory disagreeability can thus be minimized when determining the efficacy of an additive or deodorizing agent.

As various monitoring methods of hydrogen sulfide and bacterial content may be known in the art, it should be appreciated that any means for detection would be in the spirit of the invention and the invention is in no way limited to any specific detection means for either bacteria or hydrogen sulfide.

Surrogate Waste Media

Acceptable surrogate or synthetic waste compositions provide the nutrients and physical properties that would similarly be found in normal or naturally occurring waste matter, but without the same potential hazard of exposure to potentially harmful microorganisms. The most important components of waste matter comprise nitrogen/protein, minerals, vegetable fiber, consistent moisture, and waste paper pulp. The use of consistent source materials and compositions provide a reproducible performance to allow comparable tests run for differing time lengths and comprising differing additives to control odor.

It is a general objective to provide a consistent and reproducible bacterial presence in the synthetic waste water media that is similar to natural waste. It is most preferable that relatively harmless bacteria be used in the synthetic waste for reasons of safety and the general improvement over testing with natural waste matter. *Escherichia coli* K12 is the most preferable bacteria for these purposes.

We have found in the examples below that the *E. Coli* bacteria reproduce from an initial content of about $10^5$ to become about $10^8$ in five days. This system compares favorably with real world actual waste matter degradation rates whereby the odor will become very noticeable if not unacceptable in about two days and require dumping by or before the fifth day.

Hydrogen sulfide levels started at 0 ppm and increased to greater than 280 ppm in 5 days without the benefit of outside influences, treatments, additives or deodorizers. At 5 ppm the odor was found to essentially be at the maximum of acceptability.

Synthetic Waste Water Media and Efficacy Protocol

The effectiveness of various types of waste water tank deodorizers will be evaluated through the following examples. Example 1 relates to inhibitive deodorizers. Inhibiting deodorizers do not substantially prohibit the growth of odor generating bacteria. The effectiveness of an inhibiting deodorizer is evaluated by its ability to slow or delay the production of hydrogen sulfide, one of the most odoriferous gases produced by waste media.

Example #2 relates to deodorizers which are bactericidal to odoriferous gas generating organisms, such as the *E. Coli* within waste media. The effectiveness of a bactericidal deodorizer is evaluated by its ability to prevent bacterial growth.

EXAMPLE 1

Inhibitive Efficacy

Inhibitive Evaluation Procedure for Deodorizer Effectiveness for RV or Marine Waste Water Collection Tanks An experiment was conducted to evaluate the effectiveness of recreational vehicle (Black) waste water tank deodorizer in preventing aerobic degradation processes that result in unpleasant odors. The effectiveness of the tank deodorizer was evaluated through the inhibition of growth using an *E. Coli* within a synthetic waste water media. This comparison of the respective products inhibition was over selected time periods from 5 to 7 days.

Equipment & Supplies:
1. Waste water Tank/Digester Test Vessel: 1500 ml stoppered flask, or one gallon size plastic bottles with caps, or any suitable container with closure.
2. 1000 ml beakers for mixing materials
3. 20×150 mm test tubes
4. 2.0 ml disposable pipettes
5. TGY Agar Plates: also known as Standard Plate Count Agar or Standard Methods Agar.
6. Nutrient Broth (preferred) is a general purpose medium for cultivation of microorganisms with non-specific nutritional requirements. Any suitable nutrient media, specific to the requirements of the organism being used may be utilized in this procedure, i.e. LB Broth for propagation and maintenance of *E. coli*.
7. Monitor for hydrogen sulfide gas. Any meter designed to read hydrogen sulfide in parts per million (ppm).
8. Monitor holding cradle: any device for holding the monitor in a steady and reproducible position while taking head space gas readings at the immediate opening of the waste water vessel.

500 grams total of synthetic soil media was prepared having the following ingredients:
   Water (tap water) . . . 400.0 g
   Peptone (Bacto Peptone) . . . 23.7 g
   Beef extract, desiccated . . . 16.0 g.
   Urea . . . 8.8 g.
   Sodium Chloride . . . 2.0 g
   Calcium Chloride*$2H_2O$ . . . 1.0 g
   Magnesium Sulfate*$7H_2O$ . . . 0.5 g
   $K_2HPO_4$ . . . 8.0 g
   Oatmeal . . . 35.0 g
   RV biodegradable toilet paper (small pieces) . . . 5.0 g
   With the exception of the oatmeal and toilet paper, the above ingredients were mixed together and heated to 55° C. with constant mixing for 15 to 20 minutes. The oatmeal and toilet paper were then added and thoroughly mixed in. Mixture is allowed to cool to room temperature, then transferred to the waste water tank/digester test vessel.

Challenge Organism:

*Escherichia coli* strain K12 (ATCC 25253) was employed. K12 was a preferred organism to use as it was non-pathogenic, safe to use and highly effective for this test. Other organisms may be equally effective, but the non-pathogenic traits of this strain made it highly desirable for this testing.

Procedure:

1. To build up the count of microbes, using a 48-hour Nutrient Broth culture incubated at 37° C. of the *E. Coli* or other selected organism, the culture must be on at least the fourth consecutive 24-hour transfer before using. Have one tube of the 48-hour culture available for each of the test vessels.

2. Before inoculating the surrogate black waste water tank test vessel containing the synthetic soil media, the number of organisms being utilized was verified to achieve a range no less than a count of $\log^8$ per milliliter. Serial dilutions of the *E. coli* culture were prepared as follows:

a.) Tube
   #1. 1.0 ml organism culture+9.0 ml Nutrient Broth=1/10
   #2. 1.0 ml tube #1 dilution+9.0 ml Nutrient Broth=$1/10^{-2}$
   #3. 1.0 ml tube #2 dilution+9.0 ml Nutrient Broth=$1/10^{-3}$
   #4. 1.0 ml tube #3 dilution+9.0 ml Nutrient Broth=$1/10^{-4}$
   #5. 1.0 ml tube #4 dilution+9.0 ml Nutrient Broth=$1/10^{-5}$
   #6. 1.0 ml tube #5 dilution+9.0 ml Nutrient Broth=$1/10^{-6}$
   #7. 1.0 ml tube #6 dilution+9.0 ml Nutrient Broth=$1/10^{-7}$
   #8. 1.0 ml tube #7 dilution+9.0 ml Nutrient Broth=$1/10^{-8}$
   *Note: each dilution was thoroughly mixed before transferring to the next tube.

b.) Each dilution was plated by the pour plate method. 1.0 ml of dilution was plated with 10.0 ml TGY pour plate agar. Plates were incubated at 37° C. for 48 hrs before reading for enumeration.

3. Specified amounts of test subject deodorizer from the chart below were added to the test vessel containing the 500 grams of the synthetic soil media and mix thoroughly to assure uniform distribution.

| Amount of Test Subject | Label Usage Fluid Ounces per 40 gal |
|---|---|
| 0.195 ml/500 g Synthetic Soil Media | 2.0 Fluid Ounces/40 gal |
| 0.39 ml/500 g Synthetic Soil Media | 4.0 Fluid Ounces/40 gal |
| 0.78 ml/500 g Synthetic Soil Media | 8.0 Fluid Ounces/40 gal |
| 1.60 ml/500 g Synthetic Soil Media | 16.0 Fluid Ounces/40 gal |

4. 5.0 ml of the *E. coli* culture from step #1 were added to the test vessel and thoroughly mixed to assure uniform distribution. This brought the organism count to a range to greater than $1.0 \times 10^4$ cfu/ml in the 500 g of synthetic soil media.

5. Caps were placed on the test vessels and the vessels were stored at a temperature of 80° F. during the 5 day or more evaluation period. Note: Tests may be performed at various temperatures at the discretion of the investigator. For example, 100° F. incubation may be used to reflect very high summer temperature test environments.

All temperature variations were documented, and all test subjects and controls within the set were at the same temperature. The investigator may also wish to vary the length of the evaluation period. Again the evaluation period should remain the same for all tests within a set.

6. At 24 hrs contact time, handling was in such a manner as to minimize movement of the container and sewage inside. The cap was quickly removed from the test vessel and the holding cradle containing the $H_2S$ monitor was placed over the mouth of the test vessel for 4 minutes. During the 4 minute testing period the container was maintained as still as possible.

*Note: monitor must be zeroed before each reading taken.

7. After 4 minute of testing was completed, the monitor and cradle were removed from the mouth of the vessel and the cap replaced. Peak gas readings in ppm of $H_2S$ were recorded. Steps 6 & 7 were repeated for each test vessel in set.

8. Steps (6-7) were repeated for each of the remaining contact times of 48 hrs, 72 hrs, 96 hrs, 120 hrs. It should be noted that other times could be adopted for standardization of the protocol and that these times are simply preferred.

9. For test controls, two additional test vessels were ran, each containing 500 g of the synthetic soil media. One tank vessel contained no deodorizer for organism viability control. A second tank vessel contained a known performance deodorizer in an amount equal to its label directions to establish a baseline standard.

Reporting Evaluation Results:

Results were reported in ppm of $H_2S$ vs. the contact time.

Results greater than 5 ppm were found to be unacceptable levels of odor value. These results were taken from previous evaluations of a positive control containing no deodorizers. At any time during the 5-day evaluation period, $H_2S$ readings exceeding 5 ppm were considered beyond the endpoint for acceptable product efficacy performance.

| Actives Tested | Actives in formulation % by weight | Expected label usage (oz. product per 40 gal tank) | = | Dosage tested (ml/500 g synthetic soil media) |
|---|---|---|---|---|
| Bronopol | 4.5% | 8 oz | = | 0.78 ml |
| Hexamethylene-Tetramine | 13.0% | 8 oz | | 0.78 ml |
| Integra ® 44 | 15.0% | 8 oz | | 0.78 ml |
| Onyxide ® 200 | 30.0% | 8 oz | | 0.78 ml |
| Neolene ™ M-10 | 7.7% | 8 oz | | 0.78 ml |
| Kathon ™ CG-ICP | 3.3% | 8 oz | | 0.78 ml |
| Aqua Kem ® (control) | | 8 oz | | 0.78 ml |

Results:

| H$_2$S in ppm vs. contact times | | | | | |
|---|---|---|---|---|---|
| Test product (Actives) | 24 Hours | 48 Hours | 72 Hours | 96 Hours | 120 Hours |
| Bronopol | 0 | 0 | 0 | 0 | 0 |
| Hexamethylene-Tetramine | 2 | 2 | 48* | — | — |
| Integra ® 44 | 0 | 5 | 87* | — | — |
| Onyxide ® 200 | 0 | 2 | 13* | 93 | — |
| Neolone ™ M-10 | 0 | 0 | 0 | 22* | — |
| Kathon ™ CG-ICP | 0 | 10* | 74 | — | — |
| Aqua Kem ® (control) | 0 | 0 | 0 | 0 | 0 |
| Positive Control | 2 | 15* | 53 | — | — |

The * indicates when each active had reached the unacceptable level of odor value. The two best performing actives that were equal to or near the performance of the Aqua Kem control were the Bronopol and Neolone M-10.

Information for suppliers of active ingredients:
  Integra® 44 from International Specialty Products (ISP), 300 Delaware Avenue, Wilmington, Del. 19801
  Onyxide® 200 from Stepan Company, 22 W. Frontage Road, Northfield, Ill. 60093
  Neolene™ M-10 from Rohm & Haas Company, 100 Independence Mall West, Philadelphia, Pa. 19106
  Kathon™ CG-ICP from Rohm & Haas Company, 100 Independence Mall West, Philadelphia, Pa. 19106
  Aqua Kem® (control) from Thetford Corporation, PO Box 1285, Ann Arbor, Mich. 48106

EXAMPLE 2

Destruction of Microorganisms

Bactericidal Evaluation Procedure for Deodorizer Effectiveness for RV or Marine Waste Water Collection Tanks Objective: To evaluate the effectiveness of Recreational Vehicle (Black) Waste water Tank Deodorizers to prevent aerobic degradation processes that result in unpleasant odors.

The effectiveness of various types of waste water tank deodorizers were evaluated through their inhibition of growth using an *E. Coli* or other suitable organism within a surrogate waste water media. This comparison of the respective products inhibition was over selected time periods for 5-7 days.

Synthetic waste water media as disclosed in Example 1 was also employed in Example 2.

Challenge Organism:

*Escherichia coli* strain K12 (ATCC 25253) was employed.

Equipment & Supplies:

1. Waste water Tank/Digester Test Vessel: 1500 ml stoppered flask, or one gallon size plastic bottles with caps, or any suitable container with closure.
  2. 1000 ml beakers for mixing materials
  3. 20×150 mm test tubes
  4 2.0 ml disposable pipettes
  5. TGY Agar Plates: also known as Standard Plate Count Agar or Standard Methods Agar.
  6. Nutrient Broth (preferred) was a general purpose medium for cultivation of microorganisms with non-specific nutritional requirements. However, any suitable nutrient media, specific to the requirements of the organism being used may be utilized in this procedure, i.e. LB Broth for propagation and maintenance of *E. coli*.
  7. Letheen Broth, modified with the addition of Polysorbate 80 and Lecithin.

Procedure:

1. A 48-hour Nutrient Broth culture was incubated at 37° C. of the *E. Coli*. Culture was at least the fourth consecutive 24-hour transfer before using. One tube of the 48-hour culture was available for each of the test vessels.

2. Before inoculating the surrogate black waste water tank test vessel containing the synthetic soil media, the number of organisms being utilized was verified to achieve a range no less than a count of $\log^8$/ml. Serial dilutions of the *E. coli* culture were prepared as follows:

a.) Tube

1. 1.0 ml organism culture+9.0 ml Nutrient Broth=1/10
  #2. 1.0 ml tube #1 dilution+9.0 ml Nutrient Broth=1/10$^{-2}$
  #3. 1.0 ml tube #2 dilution+9.0 ml Nutrient Broth=1/10$^{-3}$
  #4. 1.0 ml tube #3 dilution+9.0 ml Nutrient Broth=1/10$^{-4}$
  #5. 1.0 ml tube #4 dilution+9.0 ml Nutrient Broth=1/10$^{-5}$
  #6. 1.0 ml tube #5 dilution+9.0 ml Nutrient Broth=1/10$^{-6}$
  #7. 1.0 ml tube #6 dilution+9.0 ml Nutrient Broth=1/10$^{-7}$
  #8. 1.0 ml tube #7 dilution+9.0 ml Nutrient Broth=1/10$^{-8}$
  *Note: Dilution was thoroughly mixed before transferring to the next tube.

b.) Each plate dilution was prepared by the pour plate method. Plate 1.0 ml of dilution with 10.0 ml TGY pour plate agar. Incubate plates at 37° C. for 48 hrs before reading for enumeration.

3. The same synthetic Soils Media (500 grams total) used in Example 1 was also used in this working Example.

4. A specific amount of test subject deodorizer from the chart below was introduced to the test vessel containing 500 grams of the synthetic soil media and mix thoroughly to assure uniform distribution.

| Amount of Test Subject | Label Usage Fluid Ounces per 40 gal |
|---|---|
| 0.195 ml/500 g Synthetic Soil Media | 2.0 Fluid Ounces/40 gal |
| 0.39 ml/500 g Synthetic Soil Media | 4.0 Fluid Ounces/40 gal |
| 0.78 ml/500 g Synthetic Soil Media | 8.0 Fluid Ounces/40 gal |
| 1.60 ml/500 g Synthetic Soil Media | 16.0 Fluid Ounces/40 gal |

5. 5.0 ml of the *E. coli* culture from step #1 was added to the test vessel and mixed thoroughly to assure uniform distribution. This brought the organism count to a range greater than $1.0 \times 10^4$ cfu/ml in the 500 g of synthetic soil media.

6. Serial dilutions of the waste water test vessel mixture were performed to arrive at a microbial count. Prepared as follows:

Tube
1. 1.0 gram sample+9.0 ml Letheen broth=1/10
2. 1.0 ml tube #1+9.0 ml Letheen broth=$1/10^{-2}$
3. 1.0 ml tube #2+9.0 ml Letheen broth=$1/10^{-3}$
4. 1.0 ml tube #3+9.0 ml Letheen broth=$1/10^{-4}$
6. 1.0 ml tube #5+9.0 ml Letheen broth=$1/10^{-6}$
7. 1.0 ml tube #6+9.0 ml Letheen broth=$1/10^{-7}$
8. 1.0 ml tube #7+9.0 ml Letheen broth=$1/10^{-8}$

*Note: Each dilution was thoroughly mixed before transferring to the next tube. The Letheen Broth and the TGY Agar contained inhibitors Tween 80 and Lecithin to guard against carryover effects of any preservative or antimicrobial additives in the recovery media.

7. Each sample was plated by the pour plate method. Plate 1.0 ml of sample dilution was with 10.0 ml of TGY pour plate agar. The plates were incubated at 37° C. for 48 hours before reading for enumeration.

8. The serial dilutions were repeated (steps 5 & 6) at various time intervals (0 hrs, 24 hrs, 48 hrs, 72 hrs, 96 hrs, 120 hours) to provide sufficient data of deodorizer adequacy.

9. After each time interval, rate the odor of the sewage using a scale of 1-5.
1=no smell
5=bad smell 10. The test vessel mixtures with caps or stoppers were stored at a temperature of 80-85° F. during the 5-7 day evaluation period. The vessels were stored and handled in such a manner as to minimize movement of the sewage. Note: Tests may be performed at various temperatures at the discretion of the investigator. For example, 100° F. may be used to reflect a very high summer temperature test environment. All temperature variations were documented, and all test subjects and controls within the set were at the same temperature. The investigator may also wish to vary the length of the evaluation period. Again the evaluation period should remain the same for all tests within a set.

11. For test validation, two additional test vessels each containing 500 g of the synthetic soil media (follow steps 1-3, 5-10) were prepared. One tank vessel contained no deodorizer for organism viability control. A second tank vessel contained a known performance deodorizer (Thetford Aqua Kem Deodorizer was used, supplied by Thetford Corporation, PO Box 1285, Ann Arbor Mich. 48106), in an amount equal to the label directions, to establish a baseline Computations:
Calculate % Microbial Reduction after each test interval to provide deodorizer effectiveness using the following formula:

$$\% \text{ Microbial Reduction} = \frac{\text{Initial microbial count} - \text{Final microbial count}}{\text{Initial microbial count}} \times 100$$

% Microbial reduction corresponds to odor failure levels. With only 60%-70% (or less) microbial reduction, the odor levels begins to rise to failure levels and usually rise to exceed the original starting cfu/ml count. If greater than 70% microbial reduction is achieved, the odor levels remain at acceptable levels.

Results:

| Product Tested | Actives in Product | Expected label usage (oz. product per 40 gal tank) | = | Dosage tested (ml/500 g synthetic soil media) |
|---|---|---|---|---|
| Campa-Chem ™ | Formaldehyde | 8 oz | = | 0.78 ml |
| West Marine ® | Quaternary Ammonium Compounds | 8 oz | = | 0.78 ml |
| Aqua Kem ® (control) | Formaldehyde | 8 oz | = | 0.78 ml |

Colony Forming Units (CFU) per ml vs time:

| Test Product | 0 hrs | 24 hr | 48 hr | 72 hr | 96 hr | 120 hr |
|---|---|---|---|---|---|---|
| Campa-Chem ™ | $8.0 \times 10^6$ | $2.4 \times 10^4$ | $1.96 \times 10^6$ | $5.0 \times 10^7$ | $4.4 \times 10^8$ | |
| West Marine ® | $1.08 \times 10^7$ | $1.55 \times 10^8$ | $2.96 \times 10^9$ | $3.4 \times 10^9$ | $4.0 \times 10^9$ | |
| Aqua Kem ® (control) | $7.6 \times 10^6$ | $1.44 \times 10^2$ | $1.5 \times 10$ | $3.0 \times 10$ | $2.0 \times 10^2$ | $1.96 \times 10^5$ |
| Positive Control | $8.8 \times 10^6$ | $3.1 \times 10^8$ | $1.32 \times 10^9$ | $2.2 \times 10^9$ | $3.1 \times 10^9$ | |

Percent Microbial Reduction for each time interval:

| Test Product | 24 hr | 48 hr | 72 hr | 96 hr | 120 hr |
|---|---|---|---|---|---|
| Campa-Chem ™ | 98.5% | 77.7% | 0% | 0% | 0% |
| West Marine ® | 0% | 0% | 0% | 0% | 0% |
| Aqua Kem ® (control) | 100% | 100% | 100% | 100% | 87.5% |
| Positive Control | 0% | 0% | 0% | 0% | 0% |

Odor rating vs time: where 1=no offensive odor, 5=extremely strong offensive odor

| Test Product | 24 hr | 48 hr | 72 hr | 96 hr | 120 hr |
|---|---|---|---|---|---|
| Campa-Chem ™ | 1 | 1 | 2 | 3 | 5 |
| West Marine ® | 1 | 3 | 5 | 5+ | 5+ |
| Aqua Kem ® (control) | 1 | 1 | 1 | 1 | 2 |
| Positive Control | 2 | 4 | 5 | 5+ | 5+ |

The quantitative data provided by the microbial count and % microbial reduction provides definitive and similar results to the subjective odor rating.

Product Manufacturer Information:
Campa-Chem™ Holding Tank Deodorizer and Aqua Kem® are products of Thetford Corporation, PO Box 1285, Ann Arbor, Mich., 48106
West Marine® Marine Head & Holding Tank Chemical Treatment is a product of West Marine, 500 Westridge Dr., Watsonville, Calif. 95076

We claim:

1. A method for determining the effectiveness of a waste water tank deodorizer, which comprises the steps of:
   (i) creating a synthetic waste water media as a substitute for a natural waste water media and providing a hydrogen sulfide generating microorganism;
   (ii) introducing in any order to said synthetic waste water media said hydrogen sulfide generating microorganism and a waste water tank deodorizer to be tested, and
   (iii) measuring the time or delay for the generation of hydrogen sulfide to occur beginning with combining of said hydrogen sulfide generating microorganism, said waste water tank deodorizer and said synthetic waste water media.

2. The method according to claim 1, wherein said hydrogen sulfide generating microorganism is a non-pathogenic bacterium.

3. The method according to claim 2, wherein said non-pathogenic hydrogen sulfide generating bacterium is from the family Enterobacteriaceae, enteric bacteria.

4. The method according to claim 3, wherein said non-pathogenic hydrogen sulfide generating bacterium is from bacterial family, Enterobacteriaceae, comprising the genus *Escherichia*.

5. The method according to claim 4, wherein said non-pathogenic hydrogen sulfide generating microorganism is from said genus *Escherichia*, species *coli*.

6. The method according to claim 5, wherein said non-pathogenic hydrogen sulfide generating microorganism specie is *E. coli*, strain K12 (ATCC 25253).

7. The method according to claim 1, wherein said synthetic waste water media is an aqueous media comprising at least a peptone, an animal protein extract, urea or urea-containing compound, at least one metal salt; a fiber-containing grain product and a cellulose-containing paper product.

8. The method according to claim 7, wherein said peptone of said synthetic waste water media is a member selected from the group consisting of bacto peptone, proteose peptone, soytone and tryptone.

9. The method according to claim 7, wherein said animal protein extract of said synthetic waste water media is a desiccated meat extract.

10. The method according to claim 9, wherein said desiccated meat extract of said synthetic waste water media is a member selected from the group consisting of beef extract, powdered beef heart, powdered beef liver and mixtures thereof.

11. The method according to claim 7, wherein said at least one metal salt of said synthetic waste water media is an alkali metal salt and/or alkaline earth metal salt.

12. The method according to claim 11, wherein said at least one alkali metal and/or alkaline earth metal salt is a member selected from the group consisting of sodium chloride, calcium chloride, magnesium sulfate, dibasic potassium phosphate and mixtures thereof.

13. The method according to claim 7, wherein said fiber-containing grain is derived from oats and/or corn.

14. The method according to claim 7, wherein the cellulose-containing paper product is toilet paper and/or facial tissue.

15. The method according to claim 7, wherein synthetic waste water media comprises from about 4.0 to about 6.0 percent-by-weight peptone; from about 2.0 to about 4.0 percent-by-weight meat extract; from about 1.0 to about 2.0 percent-by-weight of urea or urea-containing compound; from about 0.20 to about 0.50 percent-by-weight sodium chloride; from about 0.10 to about 0.30 percent-by-weight calcium chloride; from about 0.05 to about 0.20 percent-by-weight magnesium sulfate; from about 1.0 to about 2.0 percent-by-weight dibasic potassium sulfate; from about 6.0 to about 8.0 percent-by-weight fiber-containing grain; from about 0.5 to about 2.0 percent-by-weight cellulose-containing paper product, and sufficient water to 100 percent.

16. The method according to claim 2, wherein said hydrogen sulfide generating microorganism comprises a verified count of bacterium of at least $\log^8$ colony forming units/ml in liquid culture media.

17. The method according to claim 16, wherein said verified count of bacterium is introduced into a waste water for testing in an amount of at least 5.0 ml liquid culture per 500 grams of synthetic waste water media.

18. The method according to claim 17, wherein said amount of verified count of bacterium introduced into the waste water produces a final organism count of not less than $\log^4$ colony forming units/ml in the synthetic waste water media.

19. The method according to claim 1, wherein the concentration of waste water deodorizer introduced for testing is an amount proportional to the intended end-use amount of the product in real application; wherein a usage of about 2.0 to about 40.0 fluid ounces of deodorant per 40 gallon waste tank would equal about 0.19 to 3.91 ml of said waste water deodorant per 500 grams synthetic waste water media.

* * * * *